US012714593B2

(12) United States Patent
Moore

(10) Patent No.: US 12,714,593 B2
(45) Date of Patent: Aug. 25, 2026

(54) SLEEVE FOR PLACING ON A HUMAN PENIS

(71) Applicant: The PhalloFill Clinics, LLC, Dallas, TX (US)

(72) Inventor: William Allen Moore, Dallas, TX (US)

(73) Assignee: THE PHALLOFILL CLINICS, LLC, Dallas, TX (US)

( * ) Notice: Subject to any disclaimer, the term of this patent is extended or adjusted under 35 U.S.C. 154(b) by 0 days.

(21) Appl. No.: 18/830,695

(22) Filed: Sep. 11, 2024

(65) Prior Publication Data

US 2025/0082509 A1 Mar. 13, 2025

Related U.S. Application Data

(63) Continuation-in-part of application No. 18/367,629, filed on Sep. 13, 2023, now Pat. No. 12,109,142.

(51) Int. Cl.
*A61F 5/41* (2006.01)

(52) U.S. Cl.
CPC ........... *A61F 5/41* (2013.01); *A61F 2005/411* (2013.01)

(58) Field of Classification Search
CPC ........................... A61F 5/41; A61F 2005/411; A61F 2005/414; A61F 2/26; A61F 2250/0097
See application file for complete search history.

(56) References Cited

U.S. PATENT DOCUMENTS 844,798 A 2/1907 Hawley
3,131,691 A 5/1964 Scott
3,401,687 A 9/1968 Hood
3,939,827 A 2/1976 Brunstetter
4,589,874 A 5/1986 Riedel et al.
4,869,241 A 9/1989 Friedmann
4,995,381 A 2/1991 Marmar
5,360,390 A * 11/1994 Maanum .................. A61F 5/41 600/39
5,535,758 A * 7/1996 Hagihara ................. A61F 5/41 600/38
5,779,621 A 7/1998 Chaney
6,015,379 A 1/2000 Sachse
6,390,095 B1 5/2002 Magnusson
9,295,579 B1 3/2016 Bublick et al.
(Continued)

FOREIGN PATENT DOCUMENTS

CN 2076830 U 5/1991

OTHER PUBLICATIONS

Moore, William A., U.S. Appl. No. 18/367,629, filed Sep. 13, 2023 for "Medical Device for Placing on a Human Penis," (parent application).

(Continued)

*Primary Examiner* — Carrie R Dorna
(74) *Attorney, Agent, or Firm* — Nixon & Vanderhye P.C.

(57) ABSTRACT

A sleeve for placing on a human penis, the sleeve having a flexible sleeve wall having a proximal end and a distal end, the sleeve wall being configured and sized to extend from the just below the corona of the glans of the penis and along the body of the penis towards the base of the penis. The distal end includes a flange that extends radially outwards from an outer surface of the sleeve wall, the flange having an exterior side surface with a curved shape configured to match the shape of the corona of the glans of the penis.

21 Claims, 18 Drawing Sheets

(56) References Cited

U.S. PATENT DOCUMENTS

| | | | | |
|---|---|---|---|---|
| 9,622,902 | B1 | 4/2017 | Bublick | |
| 2005/0085788 | A1 | 4/2005 | Tomosada | |
| 2008/0076964 | A1 * | 3/2008 | Jared | A61F 5/41 600/39 |
| 2009/0113605 | A1 | 5/2009 | Nicolosi et al. | |
| 2010/0179379 | A1 * | 7/2010 | Park | A61F 5/41 600/41 |
| 2012/0016189 | A1 | 1/2012 | Gioia | |
| 2014/0073851 | A1 | 3/2014 | Gioia | |
| 2017/0135895 | A1 | 5/2017 | Jafri | |
| 2019/0060103 | A1 | 2/2019 | Fielding | |
| 2020/0360172 | A1 | 11/2020 | Smith et al. | |
| 2021/0378809 | A1 | 12/2021 | Jensen, II | |
| 2022/0331142 | A1 | 10/2022 | Paz | |
| 2023/0103972 | A1 | 4/2023 | Loria | |

OTHER PUBLICATIONS

International Search Report and Written Opinion mailed Dec. 4, 2024 in International Application No. PCT/US2024/046640, 14 pages.

Ask Grandpa Gourmet Coffees. Doctor Love's 1.5" Girth Sleeve, Translucent, Amazon.com, Sep. 9, 2023. [Retrieved on Nov. 16, 2024]. Retrieved from the internet. <URL: https://www.amazon.com/Doctor-Loves-1-5-Girth-Sleeve/dp/B0CHPJH3F4> entire document. See p. 8 of ISA/237, 5 pages.

* cited by examiner 10
20
1
5
45
PHALLOFILL
15

3
20
5
3

ODF
1
35
20
IDF
TF
30
40
50
a
25
1
5
LA
55
L
TS
IDS
ODS 10
20
5
1
4
15

8C
20
5
8C

Ø36
Ø33.91
Ø21.5
7
20
5
5
1
195
Ø26
15
Ø31

130
108
106
w
W
LA
102
104
100

130

130
100
106
108
110

130
106
102
100
108
104

114
110
112

116
120
121
118

124
122
126

SLEEVE FOR PLACING ON A HUMAN PENIS

CROSS-REFERENCE TO RELATED APPLICATION

This application is a continuation-in-part of U.S. application Ser. No. 18/367,629, filed Sep. 13, 2023, the entire contents of which is incorporated herein by reference in its entirety.

BACKGROUND & SUMMARY

Penile shaft girth enhancement is a procedure that can address aesthetic or genetic concerns. Such enhancement can be performed surgically or non-surgically. Following procedure and/or surgery, the penis is commonly wrapped with an ace bandage.

One aspect of the present technology is to provide a medical device, e.g., a sleeve, that can improve upon current treatment following a penile procedure/surgery.

The present technology relates generally to a medical device, e.g., a sleeve, for placing on a human penis, e.g., following penile enhancement procedure and/or surgery.

One aspect of the present technology is directed to a medical grade silicone sleeve or sheath structured to, for example, compress and/or elongate a penis from the base (proximal shaft) to just below the corona of the glans (head of the penis).

Another aspect of the present technology is to provide a medical device for placing on a human penis, the medical device comprising: a flexible sleeve having a proximal end and a distal end, the proximal end being sized and dimensioned to be positioned over the base of the penis, the sleeve being configured and sized to extend from the base of the penis and along the body of the penis, the distal end being sized and dimensioned to terminate just below the corona of the glans of the penis.

The distal end may include a flange that extends radially outwards from an outer surface of the sleeve, wherein the flange is about 5 mm in thickness, and wherein a thickness of the sleeve spaced away from the flange along a longitudinal axis of the sleeve is about 2 mm-3 mm, or 2.5 mm.

The thickness of the sleeve may be about 1-4 mm, e.g., 2.5 mm from the distal end to the proximal end.

The sleeve may have a wall thickness of about 0.5 to about 10 mm, e.g., about 1 mm to about 5 mm, about 2-4 mm, or 2 mm, 2.5 mm or 3 mm.

The sleeve may have an inner diameter of about 15-60 mm, or about 20-40 mm.

The sleeve may come in a variety of sizes, having an inner diameter of about 20 mm, 22 mm, 24 mm, 26 mm 28 mm, 30 mm, 32 mm, 34 mm, 36 mm or 38 mm. Larger diameters are contemplated as well, including 40 mm, 42 mm 44 mm or 46 mm.

In examples, the length of the sleeve is about 180-220 mm, or about 195 mm (which may be cut to size).

In examples, the sleeve is configured to be moved from an unrolled positioned to a rolled position by rolling the proximal end radially outwards and axially towards the distal end. In the rolled position, the sleeve is stretchable from a first diameter to a second diameter.

In examples, the sleeve is in the form of a substantially flat sheet with longitudinal edges or margins that are joined to one another at a scam.

In examples, the sleeve includes an indicator or indicia (e.g., a logo and/or arrow) to indicate what side is intended to be the superior side when in place on the penis.

In examples, the distal end includes a flange that extends radially outwards from an outer surface of the sleeve.

In examples, an inner diameter of the flange is less than an inner diameter of the distal end of the sleeve.

In examples, the flange is contained in a plane that is angled relative to a longitudinal axis of the sleeve. If no flange is provided, the sleeve can be cut or made at such an angle. The angle allows the sleeve to match a shape of the corona of the glans of the penis. The flange angle may be about 1-15 degrees, or about 4-6 degrees.

In examples, a diameter of the flange is about 2-10 mm (e.g., 4-5 mm) greater than an outer diameter of the sleeve spaced axially away from the flange.

In examples, a thickness of the flange if about 2-8 mm, e.g., about 5 mm.

In examples, the flange has a circumferential wall that defines a variable wall angle with respect to a longitudinal axis of the sleeve. For example, the wall angle varies around the circumference of the wall, with a superior portion of the wall having a superior wall angle that is different than an inferior portion of the wall.

In examples, an inner diameter of the flange includes an inwardly angled portion (e.g., in the form of a cone shape) that forms an angle relative to an inner surface of the sleeve adjacent the flange.

In examples, the sleeve is made of medical grade, biocompatible silicone, a textile and/or a thermoplastic elastomer.

In examples, the sleeve has a closed loop shape in cross section, e.g., circular, oval, or nearly oval or circular, and may have a solid wall portion from the distal end to the proximal end with no openings or interruptions. The circumference of the sleeve may be constant from the proximal end to the distal end, but the circumference could taper down (e.g., 1-2 mm) from the proximal end to the distal end.

In examples, the sleeve is configured to compress and/or elongate the penis.

In examples, the sleeve is configured to resist migration of at least one girth enhancement product injected into the penis.

In examples, the at least one girth enhancement product includes a dermal filler, fat graft, or girth enhancement device.

Another aspect of the present technology is directed to a kit for post procedural treatment for penile enhancement, including a plurality of flexible sleeves, wherein each said sleeve has a different inner diameter but substantially the same length and the substantially same thickness.

In examples, the plurality of flexible sleeves includes 2-15 said sleeves, e.g., 10 sleeves, and the plurality of sleeves may include 4-6 said sleeves.

Another aspect of the present technology is to provide a medical grade silicone sleeve or sheath structured to compress and/or elongate a penis from the base or proximal shaft of the penis to just below the corona of the glans or head of the penis.

Another aspect of the present technology is directed to a sleeve for placing on a human penis, the sleeve having a flexible sleeve wall having a proximal end and a distal end, the sleeve wall being configured and sized to extend from the just below the corona of the glans of the penis and along the body of the penis towards the base of the penis. The distal end includes a flange that extends radially outwards from an outer surface of the sleeve wall, the flange having an exterior side surface with a curved shape configured to match the shape of the corona of the glans of the penis.

Another aspect of the present technology is directed to a device for placing on a human penis, the device consisting of a flexible sleeve consisting of a single layer of homogeneous material, the sleeve having a proximal end and a distal end, the sleeve not covering the head of the penis and being configured and sized to extend from the corona of the glans of the penis and along the body of the penis towards the base of the penis. The distal end may include a flange that extends radially outwards from an outer surface of the sleeve, and a wall thickness of the sleeve spaced away from the flange along a longitudinal axis of the sleeve may be about 0.5 mm to about 10 mm from the distal end to the proximal end, not including the flange. The flange may be contained in a plane and the plane is angled about 1-15 degrees relative to the longitudinal axis of the sleeve. The sleeve may be made of silicone.

Another aspect of the present technology is directed to a device for placing on a human penis, the device comprising a flexible sleeve having a proximal end and a distal end, the distal end being sized and dimensioned to extend just below the corona of the glans of the penis towards the base of the penis, wherein the sleeve from the distal end to the proximal end has a closed loop shape in cross section, and has a solid wall portion with substantially no openings or interruptions, wherein the sleeve has a longitudinal axis and is rollable along the longitudinal axis, wherein the distal end includes a flange that extends radially outwards from an outer surface of the sleeve, wherein the flange is about 2-8 mm in thickness, and wherein a thickness of the sleeve spaced away from the flange along a longitudinal axis of the sleeve is about 0.5 mm to about 10 mm, and wherein an outer diameter of the flange is about 2-10 mm greater than an outer diameter of the sleeve wall spaced axially away from the flange.

This disclosure will now provide a more detailed and specific description that will refer to the accompanying drawings. The drawings and specific descriptions of the drawings, as well as any specific or alternative examples discussed, are intended to be read in conjunction with the entirety of this disclosure. The medical device may, however, be embodied in many different forms and should not be construed as being limited to the examples set forth herein; rather, these examples are provided by way of illustration only and so that this disclosure will be thorough, complete, and fully convey understanding to those skilled in the art. Moreover, one or more features of one example may be used in conjunction with any and all of the alternate examples.

DETAILED DESCRIPTION OF EXAMPLE NON-LIMITING EXAMPLES

The present technology is directed to medical device configured to be worn by a human. In an example, the medical device is in the form of a sleeve or a sheath configured to cover a portion of a human penis, e.g., following a procedure, e.g., a surgical procedure. However, the sleeve or sheath can also provide benefits to a user even if the user has not been subject to a procedure or surgery. For example, the sleeve can provide some widening and/or lengthening on its own and/or prevent some retraction even if the user has not been subject to a procedure or a surgery.

In addition, the sleeve may be worn by a user to increase confidence, by providing the appearance that the user's penis is larger than it actually is in a natural way, e.g., as seen through clothing such as bathing suits, underwear, pants or shorts, etc.

Figures 1, 2, 3:
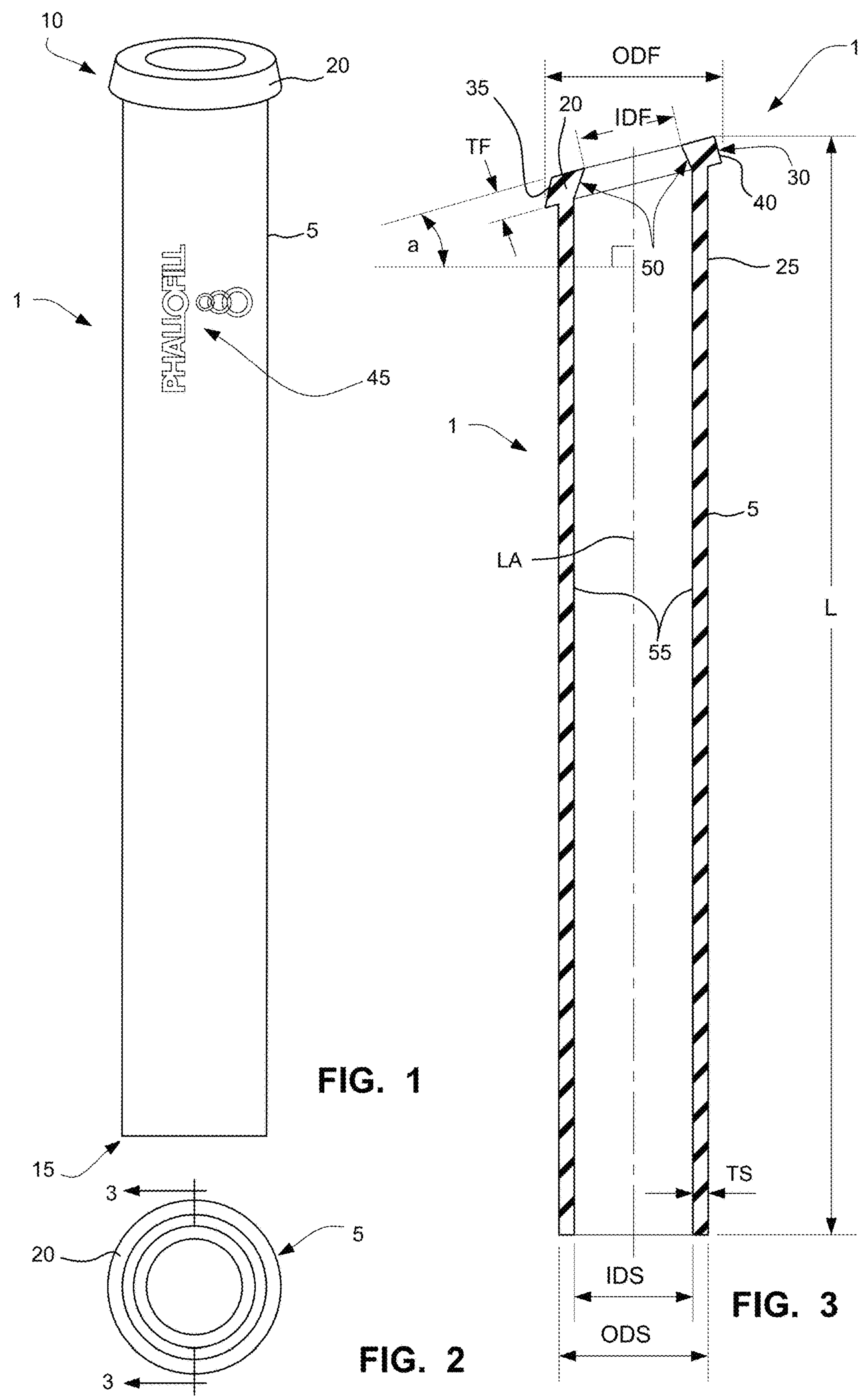
FIG. 1 is a front view of a medical device according to an example of the present technology.
FIG. 2 is a bottom view taken from the proximal end of the medical device shown in FIG. 1
FIG. 3 is a cross-sectional view taken along line 3-3 of FIG. 2.

FIG. 1 illustrates a front view of a medical device 1, which may take the form of a sleeve 5 (or sheath). The sleeve 5 may include a distal end 10 and a proximal end 15. The proximal end 15 is sized and configured to be positioned over the base of the penis. The sleeve 5 is configured and sized to extend from the base of the penis and along the body of the penis. The distal end 10 is sized and configured to terminate just below the corona of the glans of the penis, as seen, for example, in FIGS. 4E-4F.

The sleeve may have a closed loop shape in cross section, as seen in FIGS. 2 and 3. The sleeve 5 may have a solid wall portion from the distal end to the proximal end, e.g., with substantially no openings or interruptions.

The distal end may include a flange 20 that extends radially outwards from an outer surface 25 of the sleeve 5.

Dimensions and/or Geometry

The thickness TS of the sleeve 5 is about 0.5 mm to about 10 mm from the distal end to the proximal end, not including the flange 20. In examples the thickness is about 1 mm to about 4 mm. The thickness may be about 2-3 mm, or 2.5 mm. The thickness TS could vary based on the diameter of the sleeve 5, or the thickness can remain constant regardless of the diameter (e.g., inner diameter IDS) of the sleeve, as described in relation to the kit of sleeves below. This thickness (e.g., 2.5 mm) or range of thicknesses has been found to be beneficial, e.g., in terms of allowing the sleeve to be manipulated and/or providing medical benefits to the user, as described herein. For example, this thickness allows for the sleeve to be rolled and stretched during placement on the penis, and also allows nocturnal erections (expansion) yet is still firm or rigid enough to hold the penis extended without having folds or "wrinkles" in the sleeve. The sleeve may be relatively more rigid in the axial direction, and relatively more flexible in the circumferential direction. Sleeves with thicknesses outside this range (e.g., below 2 mm or above 4 mm) can still be used, but may not work as well. In addition, the thickness TS of the sleeve 5 could vary along the longitudinal axis LA, e.g., the thickness at the proximal end could be more than the thickness at the distal end, and gently tapered therebetween.

The inner diameter IDS of the sleeve is about 15-50 mm, or it may be about 20-40 mm. The inner diameter IDS may be 20 mm, 22 mm, 24 mm, 26 mm 28 mm, 30 mm, 32 mm, 34 mm, 36 mm or 38 mm. Larger sizes are available as well, including 40 mm, 42 mm, 44 mm, 46 mm, etc.

A length L of the sleeve is about 180-220 mm, e.g., about 195 mm.

The flange 20 is contained in a plane P that is angled at a flange angle a relative to a longitudinal axis LA of the sleeve 5. The flange angle a is about 1-15 degrees, or about 3-6 degrees. The angle is selected to match the shape of the corona of the glans of the penis. If no flange is provided, the distal end of the sleeve is preferably angled to so match.

An outer diameter ODF of the flange 20 is about 2-10 mm, e.g., 4-5 mm, greater than the outer diameter ODS of the sleeve, spaced axially away from the flange 20. In an example, an inner diameter IDF of the flange 20 is less than an inner diameter IDS of the distal end 10 of the sleeve 20. Making the inner diameter less than the sleeve diameter should help to prevent the head of the penis from retracting into the sleeve.

In an example, a thickness TF of the flange 20 is about 2-8 mm, e.g., about 5 mm.

The flange 20 has a circumferential wall 30 that defines a variable wall angle with respect to the longitudinal axis LA of the sleeve. The wall angle varies around the circumference of the wall 30, e.g., with a superior portion 35 of the wall having a superior wall angle that is different than an inferior portion 40 of the wall.

In this context, the superior portion of the sleeve may be marked with an indicator or indicia 45, e.g., a logo and/or an arrow, to help the user or physician mount the sleeve 5 in the correct position on the user's penis. For example, the indicia 45 is positioned about a superior (top) surface of the penis that faces upwards when the user is in a standing position. The indicia 45 helps to align the flange 20 in the correct position relative to the corona of the glans of the penis. In another example, the indicia may be a line on the inner surface of the sleeve that is revealed when the sleeve is rolled. In another example, the top surface of the flange may include an alignment mark or arrow, as the flange is always visible even if the sleeve is rolled.

The inner diameter IDF of the flange 20 includes an inwardly angled portion 50 that forms an angle relative to an inner surface 55 of the sleeve adjacent the flange. In an example, the angled portion 50 forms a part of a cone, e.g., a truncated cone having a base diameter that is greater than the top diameter. In an example, the cone is asymmetric. The cone shape helps to prevent the penis from retracting into the sleeve.

Fitting the Sleeve

In an example, the sleeve 5 is configured to be moved from an unrolled position (e.g., FIGS. 1-3) to an at least partly rolled position (FIGS. 4A-4E) by rolling the proximal end 15 radially outwards and axially towards the distal end 10.

Figure 4A:
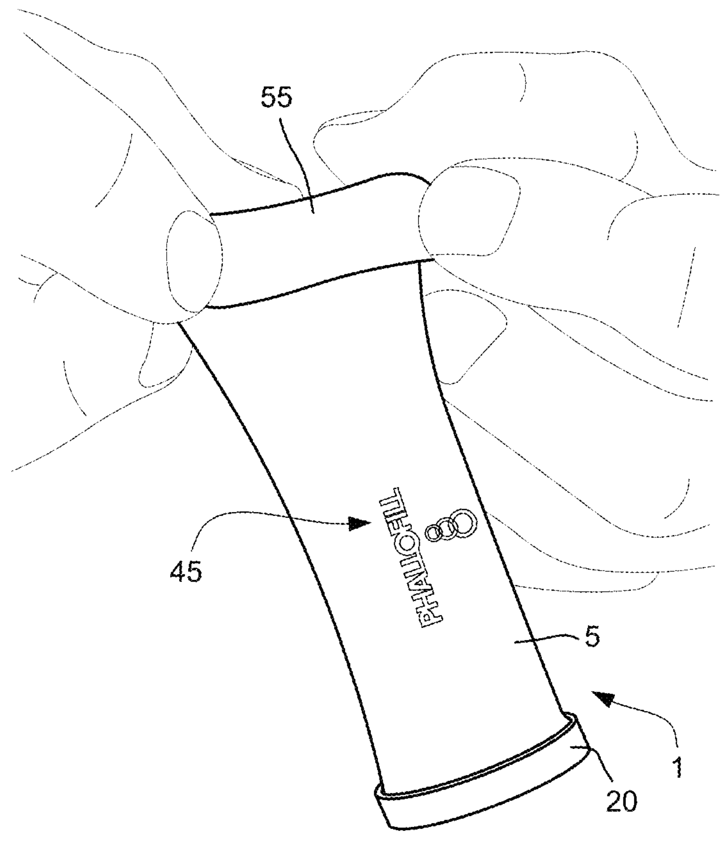
FIGS. 4A-4F illustrate an example of how the medical device of the present technology is applied to a model human subject.
Figure 4B:
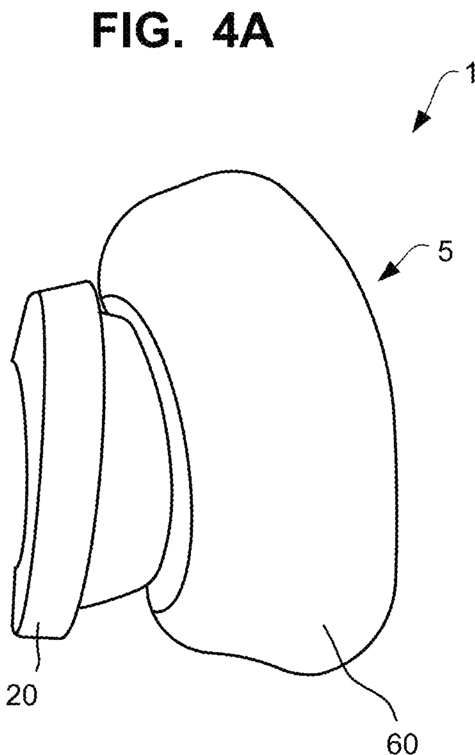

In the position shown in FIG. 4A, the user or physician begins to roll the proximal end 15, e.g., by turning the sleeve 5 inside-out, such that the inner surface 55 is exposed and rolled over the outer surface 25 It should be noted that prior to commencing the rolling operation, the user or physician may choose to cut the sleeve 5 to a length that is suitable for the given user or patient.

Figure 4C:
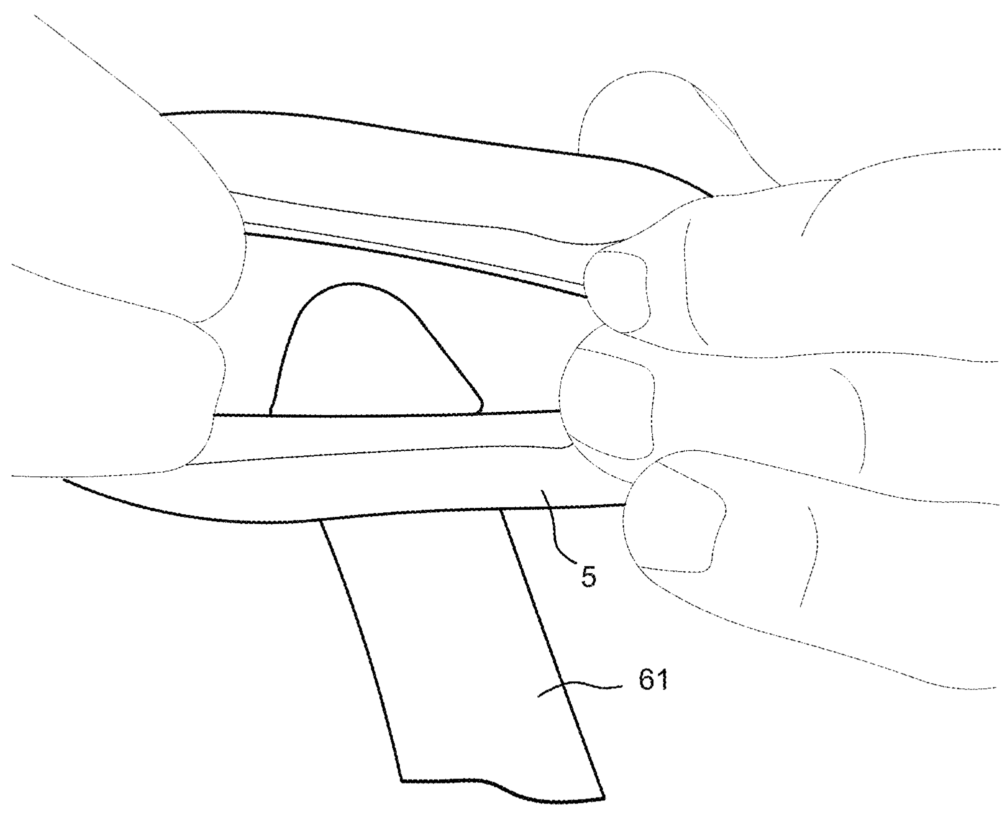

The user or physician continues to roll the sleeve 5 until the rolled part 60 is adjacent to or abuts the flange 20. In the rolled position of FIG. 4B, the sleeve 5 is stretchable from a first diameter (FIG. 4B) to a second diameter (FIG. 4C). For example, the sleeve should be stretchable to a diameter that is from 10-200% (e.g., 25-50%) of the rolled diameter in FIG. 4B. This helps avoid discomfort when passing the penis through the hollow sleeve 5.

Figure 4D:
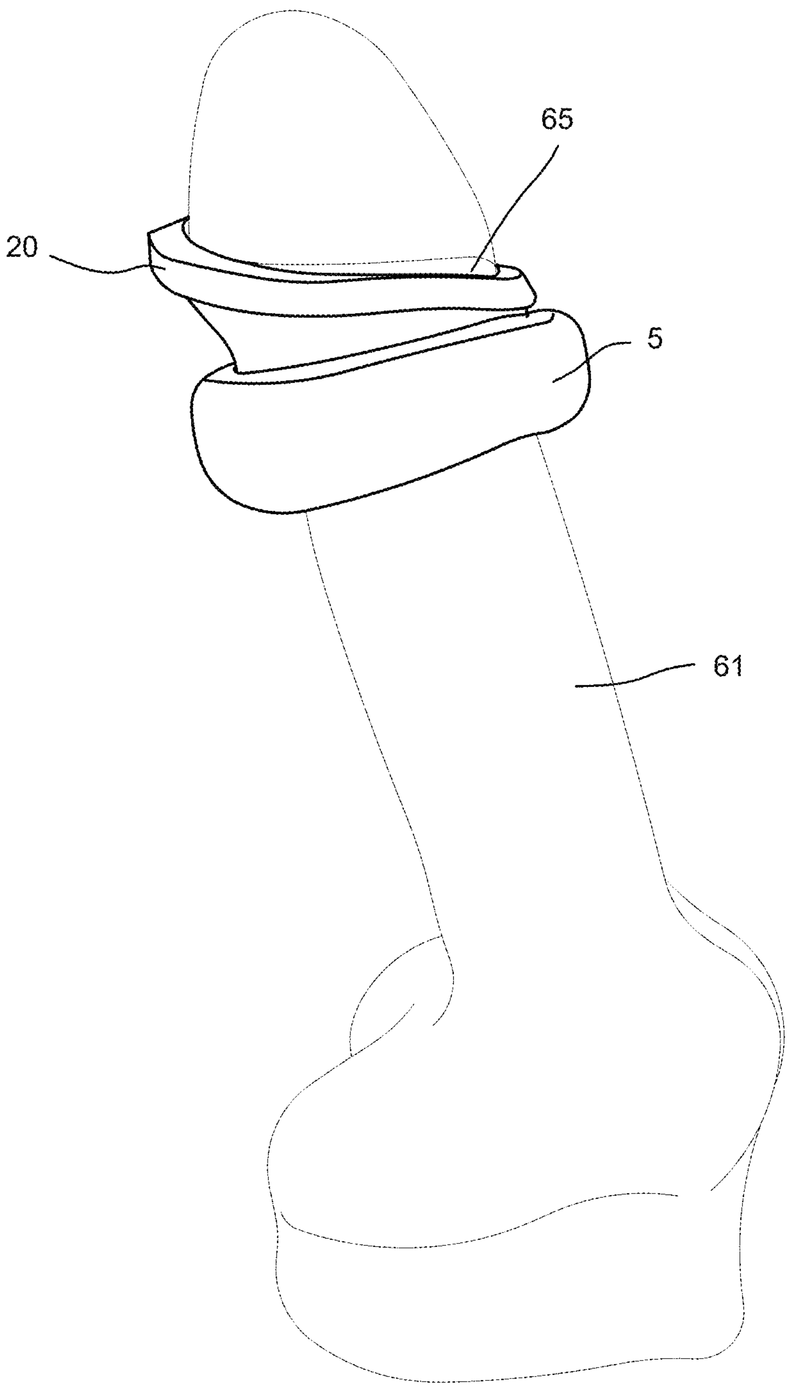

In FIG. 4D, the sleeve in its rolled up position is shown as being fit over a model penis 61, with the logo or indicia 45 positioned on the superior side of the penis. Thus the angle of the flange 20 substantially matches the angle of the corona 65 of the glans of the penis.

Figure 4E:
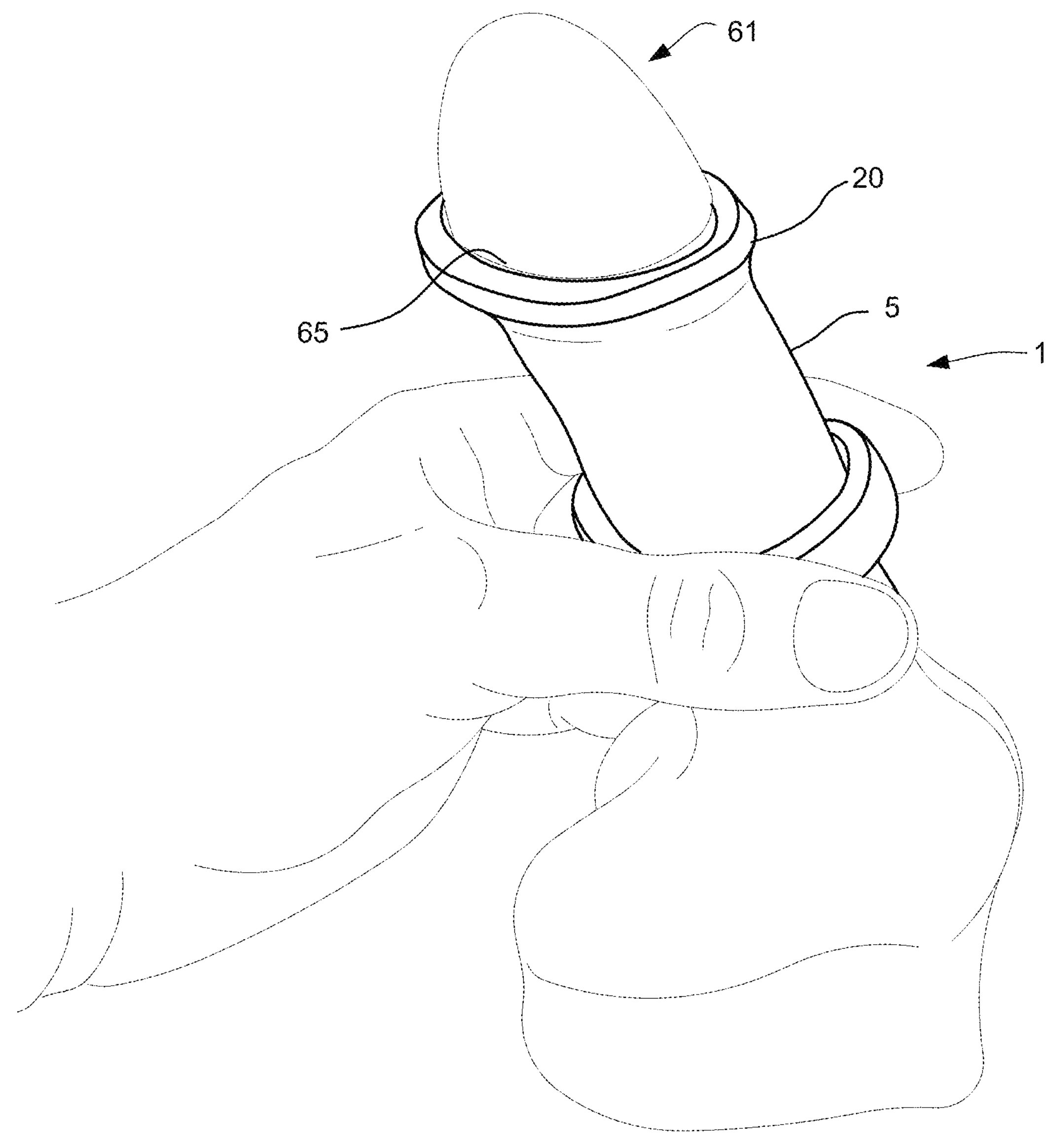
Figure 4F:
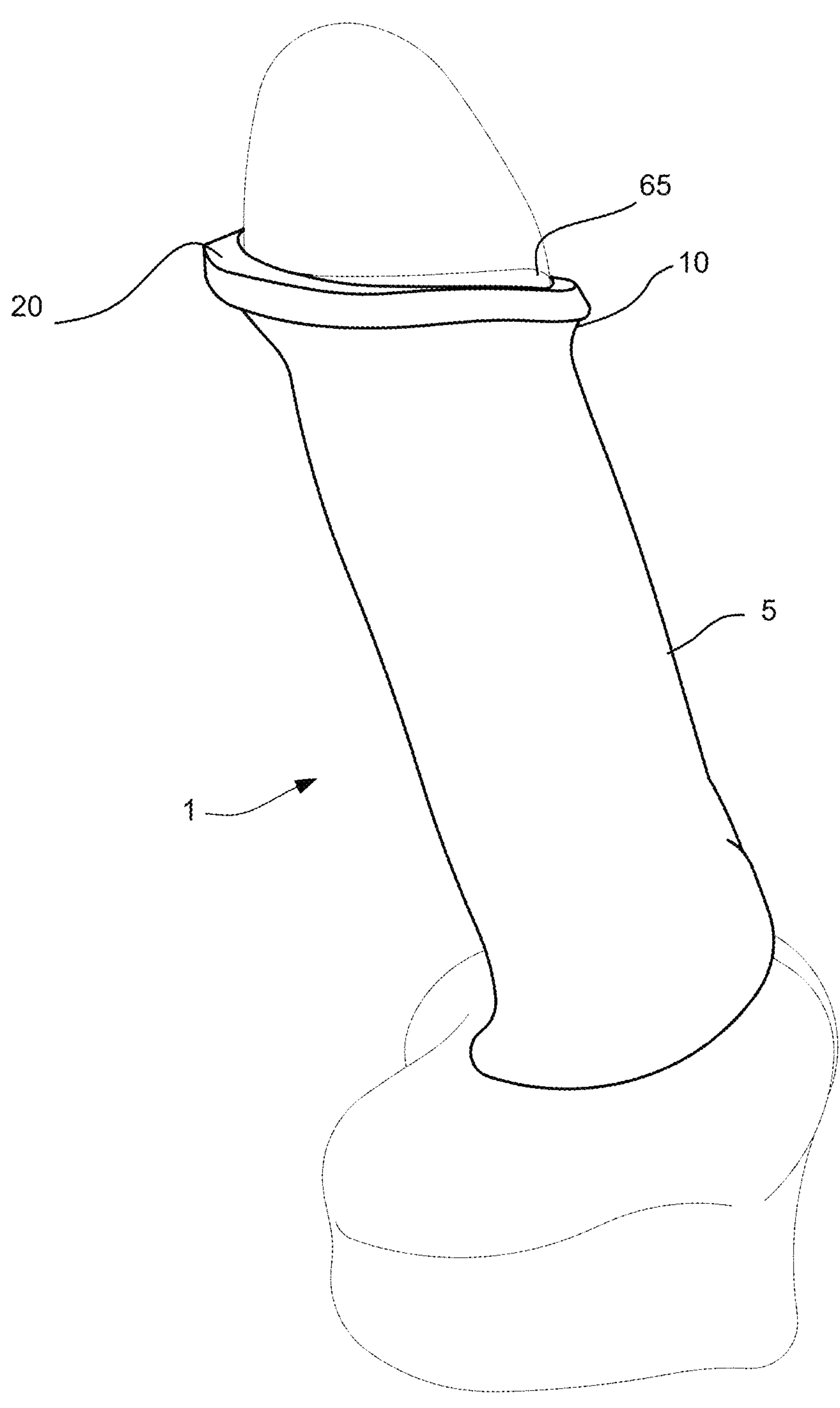
Figures 5A, 5B, 5C:
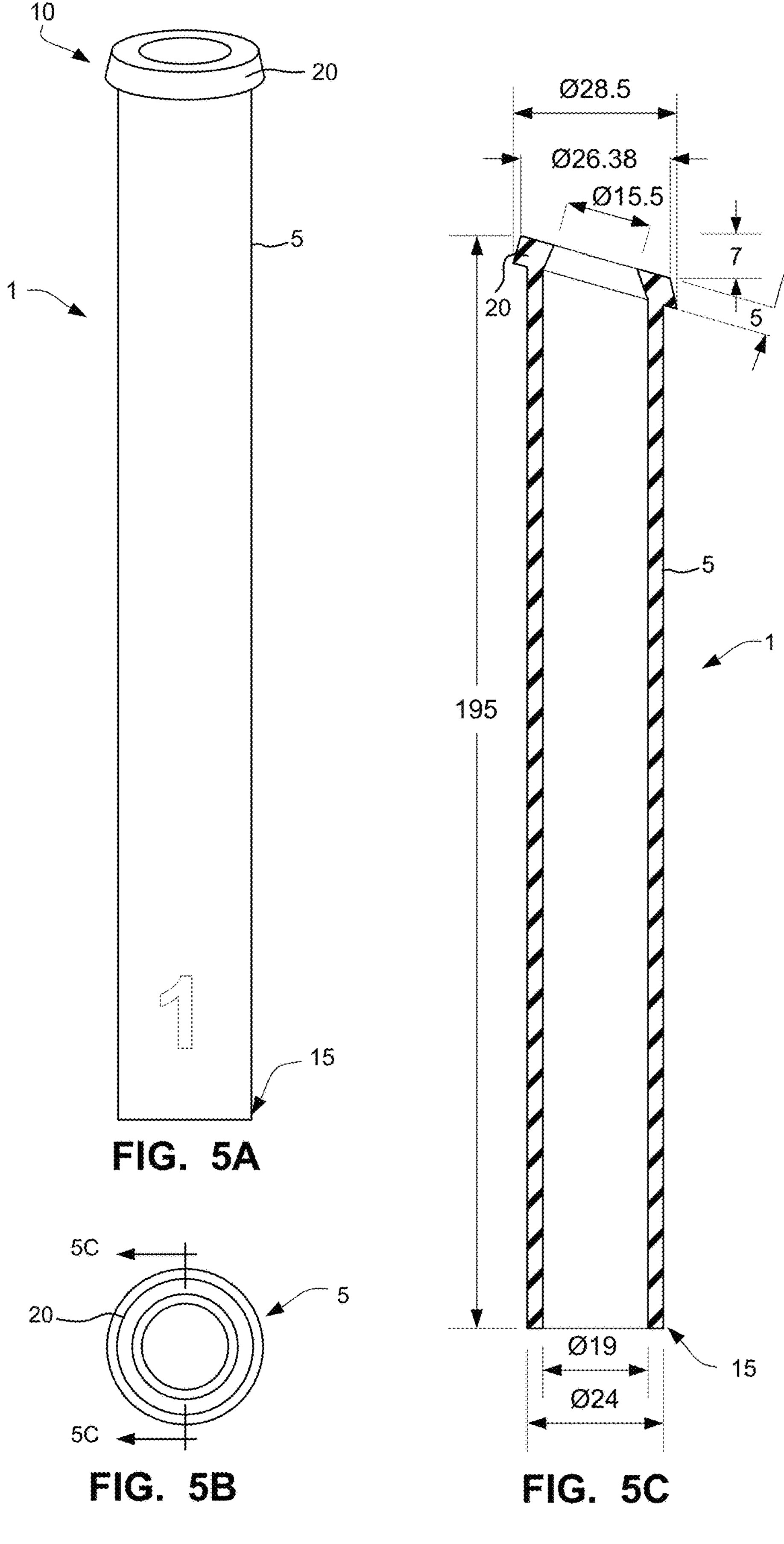
FIGS. 5A-5C illustrate views of a first size of a medical device according to an example of the present technology.

In FIG. 4E, the user or the physician (or clinician) rolls the sleeve 5 down towards the pubic bone or area of the user, and FIG. 4F shows the sleeve 5 in a completely unrolled state.

In the position shown in FIG. 4F, the sleeve 5 is configured to compress and/or elongate the penis, as the sleeve has a resiliency that tends to return the sleeve to its relaxed position (FIG. 1). The sleeve does not return to its fully relaxed position when in use, but instead is in a stretched position when in the "in use" position shown in FIG. 4F, e.g., 3-20%, e.g., 5-10%, to have the intended effect. Such circumferential compression of the shaft of the penis (when the sleeve wall is in tension due to stretch) also may help to keep the head of the penis from retracting into the sleeve.

To remove the sleeve, it may be cut along the axis with medically safe scissors, or the sleeve can be rolled back up (either direction, but preferably from the proximal end towards the distal end) whilst on the penis, and then stretched to overcome the head of the penis.

The sleeve is configured to resist migration of at least one girth enhancement product injected into the penis. The at least one girth enhancement product may include a dermal filler, fat graft, or girth enhancement device.

Materials

In an example, the sleeve is made of a rubber or elastic material, e.g., medical grade silicone or a thermoplastic elastomer. Table 1 below provides exemplary properties of the sleeve, e.g., the medical grade silicone, including hardness, density, resilience, tensile strength, tear strength, elongation and permanent set. The standard value represents a suitable range, which may vary from 5 to 20%, e.g., 8-12%. Test Standard, Unit and Test Value are also identified for each Testing Item in Table 1.

TABLE 1

| Testing Items | Test Standard | Unit | Standard Value | Test Value |
|---|---|---|---|---|
| Hardness | GB/T 531.1-2008 | Shore A | 2-5 | 3 |
| Density | GB/T 533-2008 | $g/m^3$ | 1.07 ± 0.02 | 1.06 |
| Resilience | GB/T 1681-2009 | % | 25-35 | 25 |
| Tensile Strength | GB/T 528-2009 | MPa | 1-4 | 1.1 |
| Tear Strength | GB/T 529-2008 | kN/m | 5-20 | 6.8 |
| Elongation | GB/T 528-2009 | % | 700-900 | 853 |
| Permanent Set | GB/T 528-2009 | % | 1.7-4.3 | 4.3 |

The material, one or more of the properties shown in Table 1, geometry and/or one or more of the dimensions of the sleeve as described herein at least partly allow the sleeve to operate as described and/or provide the beneficial effects described herein.

The sleeve may be transparent or opaque. The sleeve may be customizable and include the patient's monogram or other customized features, such as a specific design or wording. The sleeve may come in a variety of colors, e.g., to match the skin of the patient.

The sleeve may be made of an elastic material, as described above. However, the sleeve may also be made of a textile material and/or an elastic material, e.g., a composite material having both textile and elastic materials. Textile materials can be made of resilient, stretchy material to allow the sleeve to apply compression to the penis when worn. Textile materials may be breathable, which might be beneficial to healing and comfort. Similarly, an elastic sleeve could be provided with perforations to allow for breathability.

Moreover, the sleeve may be manufactured to stretch in the circumferential direction, yet be relatively less stretchy in the axial direction. This can be accomplished by using rigidizers or textile threads that extend in the longitudinal direction, but not in the circumferential direction. In the circumferential direction, elastic threads may be provided to provide for the desired degree of stretch.

Kit

Figures 6A, 6B, 6C:
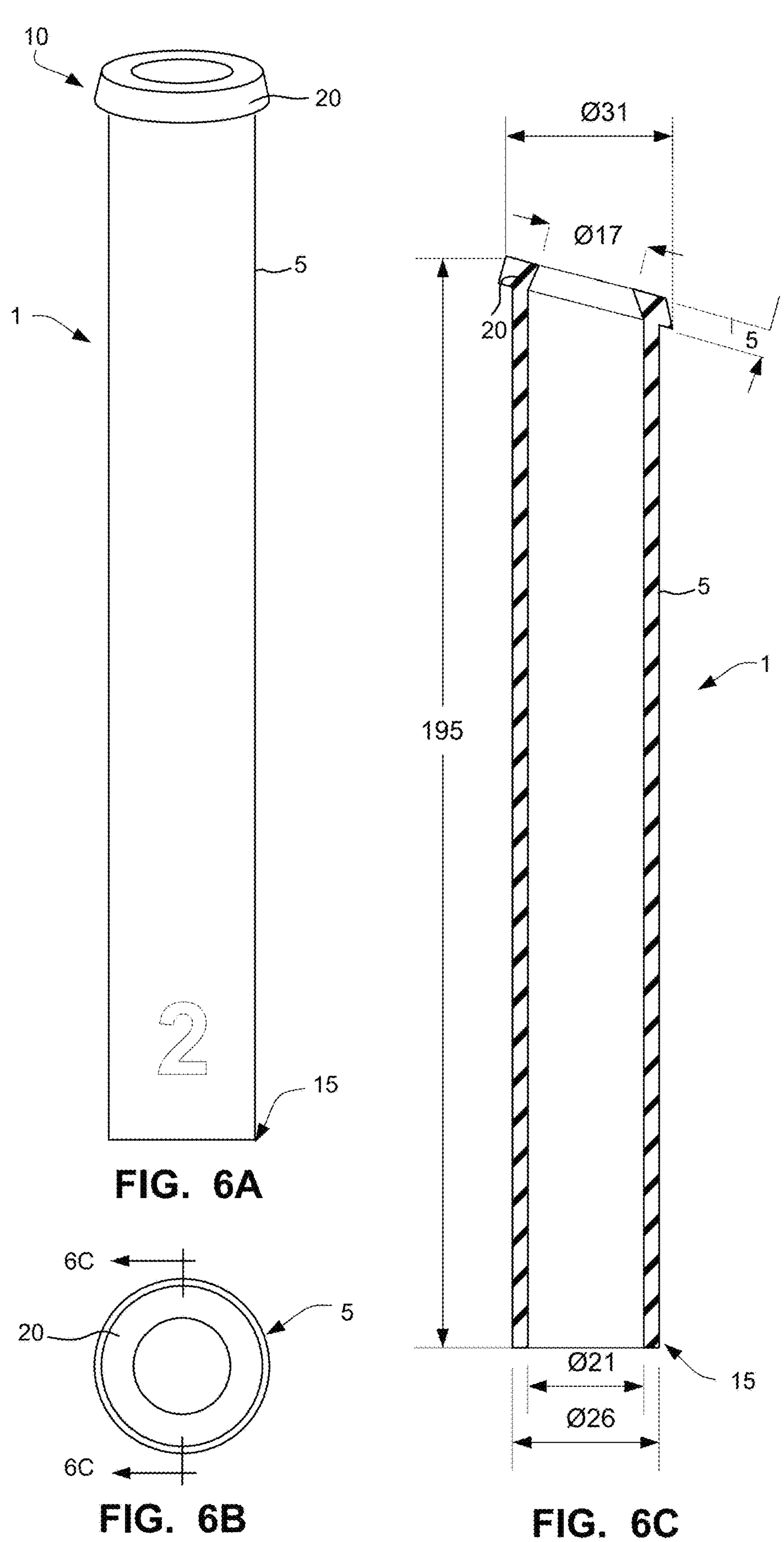
FIGS. 6A-6C illustrate views of a second size of a medical device according to an example of the present technology.
Figures 7A, 7B, 7C:
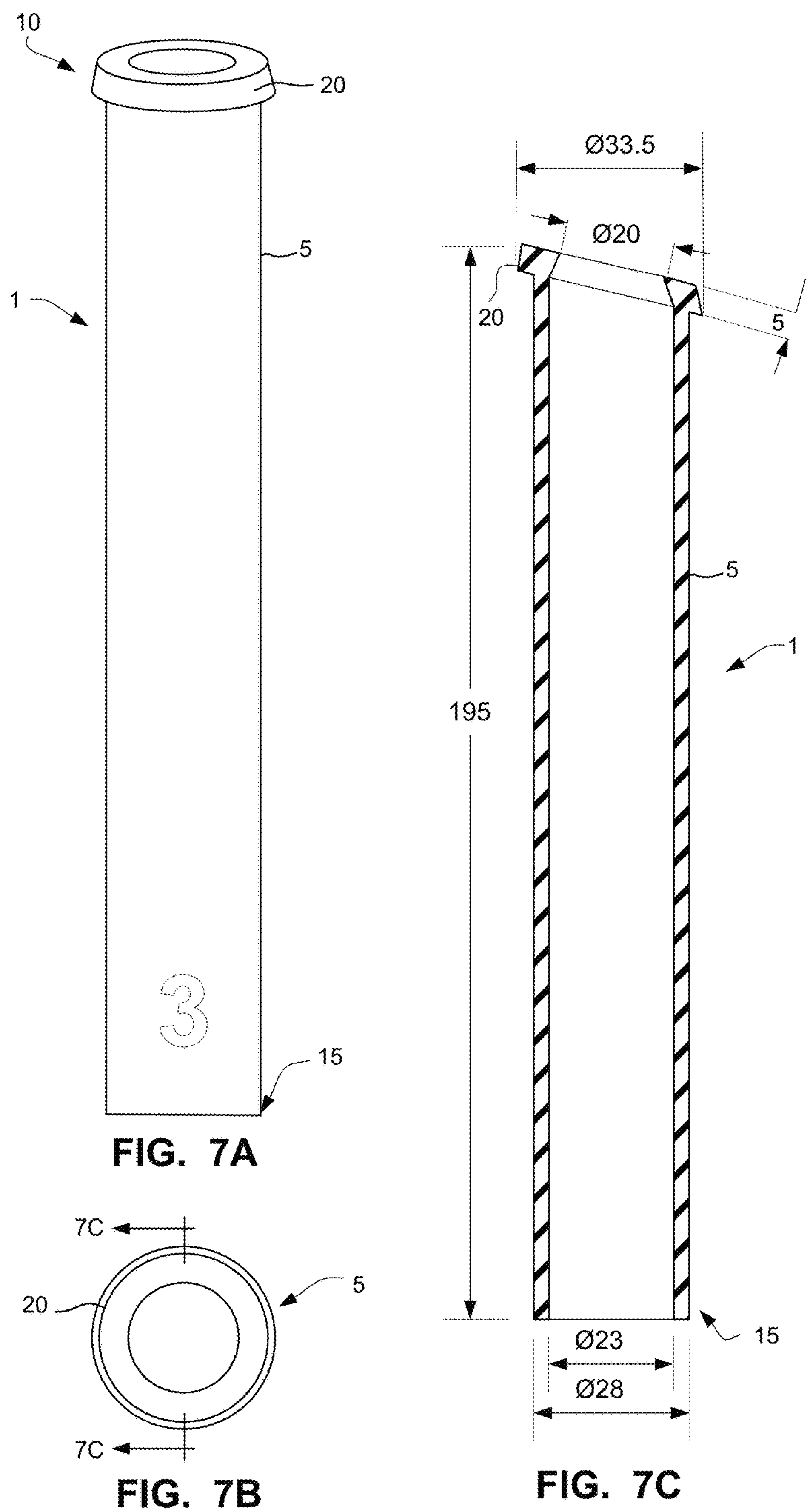
FIGS. 7A-7C illustrate views of a third size of a medical device according to an example of the present technology.
Figures 8A, 8B, 8C:
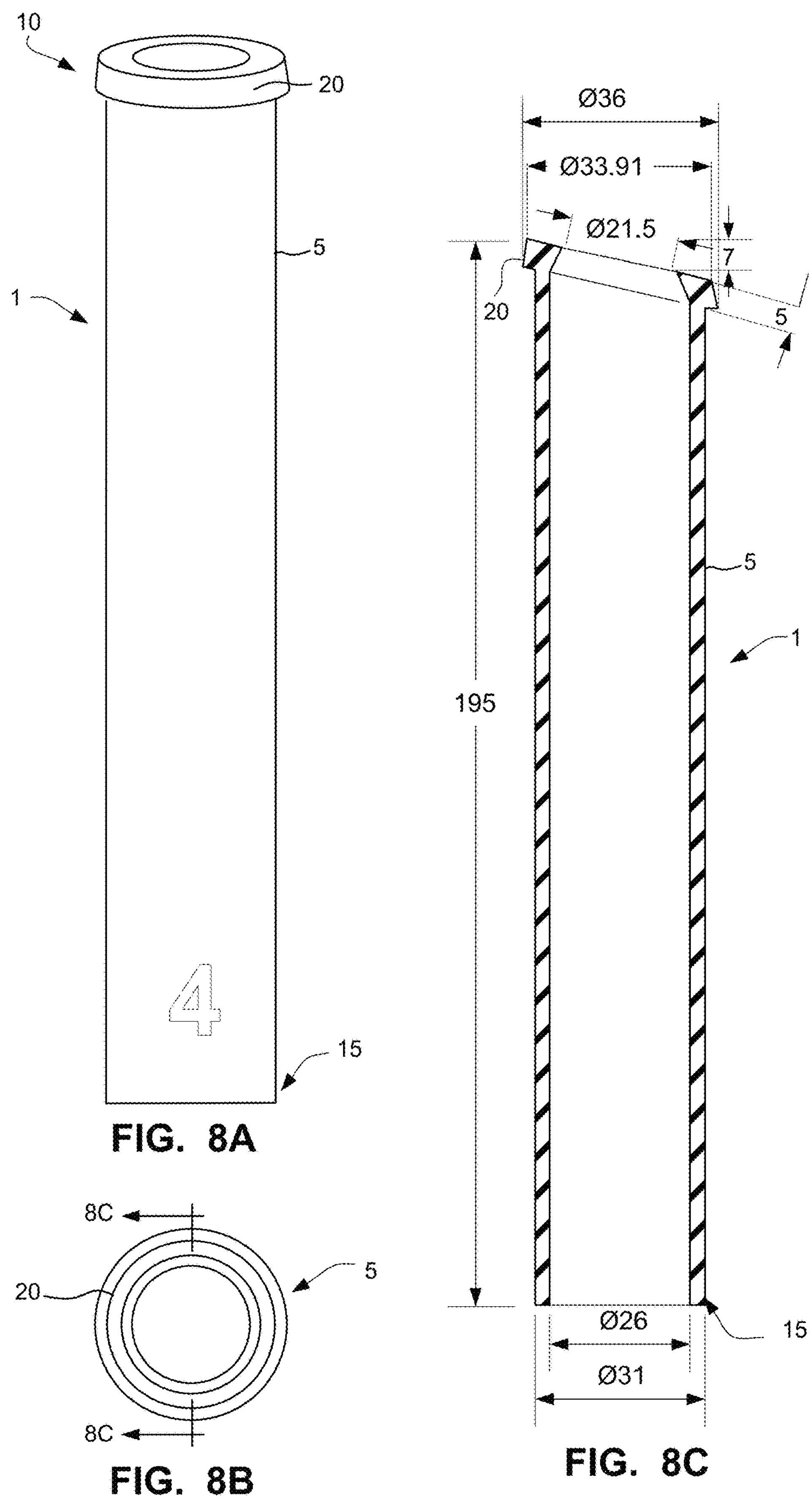
FIGS. 8A-8C illustrate views of a fourth size of a medical device according to an example of the present technology.
Figures 9A, 9B, 9C:
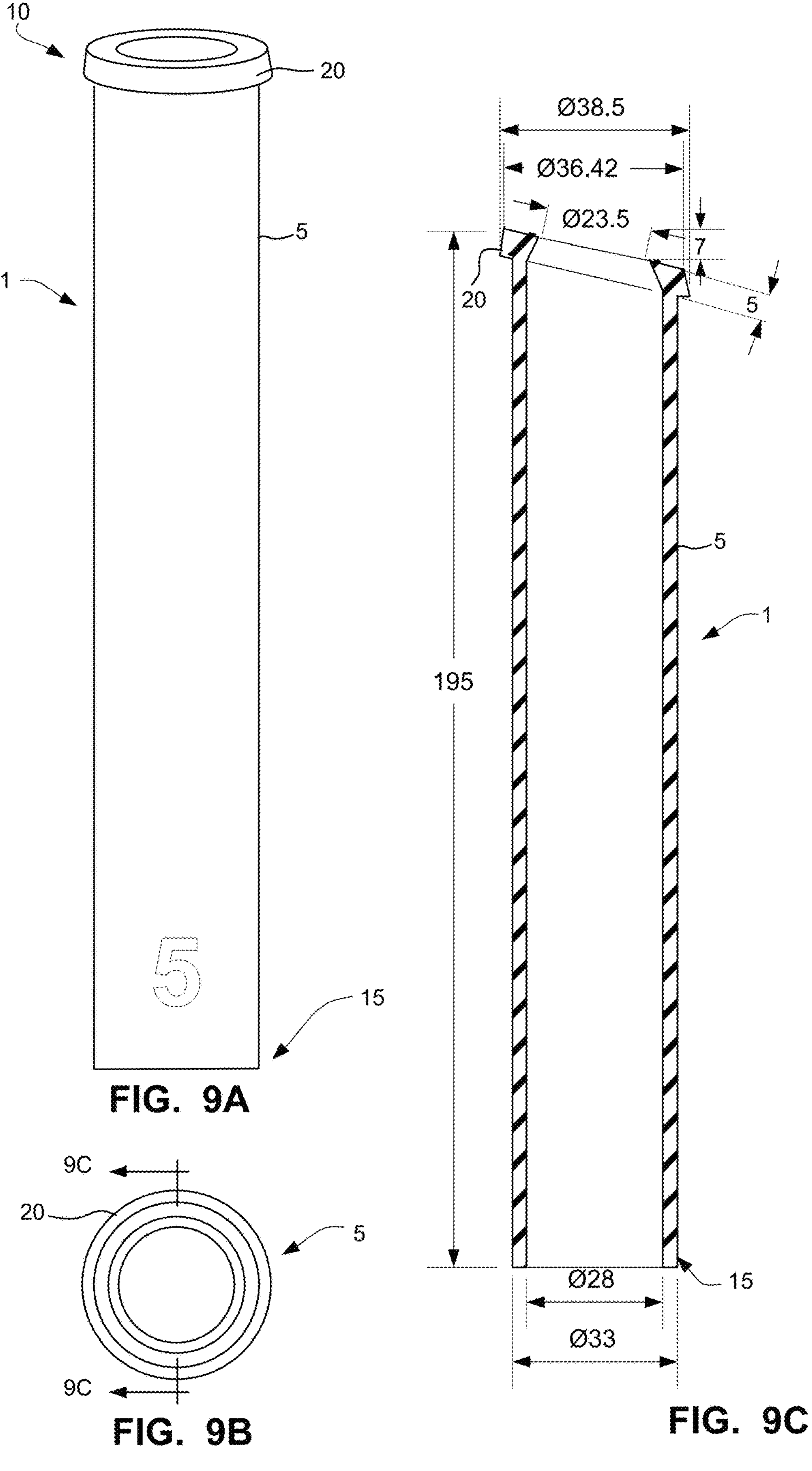
FIGS. 9A-9C illustrate views of a fifth size of a medical device according to an example of the present technology.
Figures 10A, 10B, 10C:
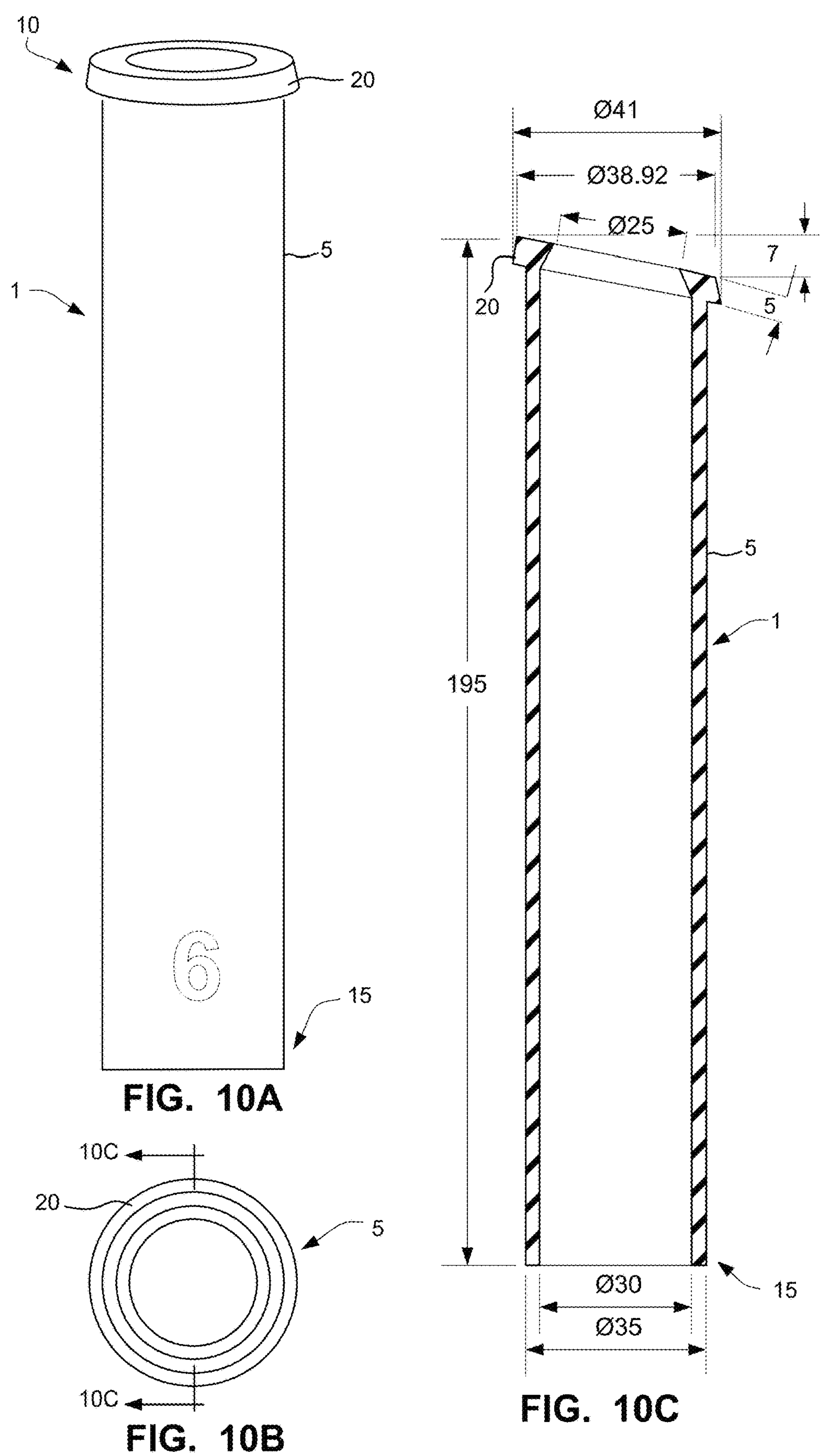
FIGS. 10A-10C illustrate views of a sixth size of a medical device according to an example of the present technology.
Figures 11A, 11B, 11C:
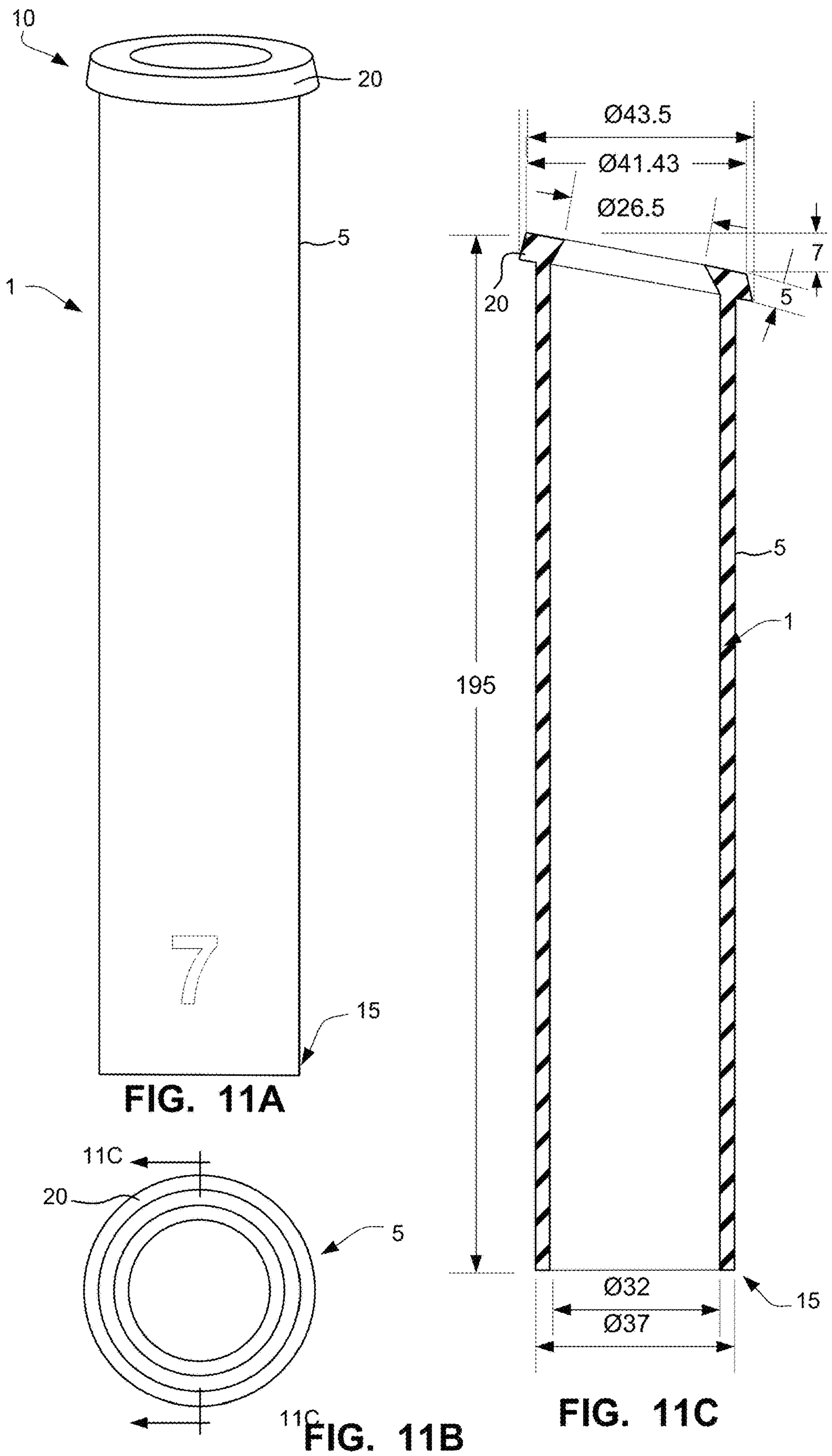
FIGS. 11A-11C illustrate views of a seventh size of a medical device according to an example of the present technology.
Figures 12A, 12B, 12C:
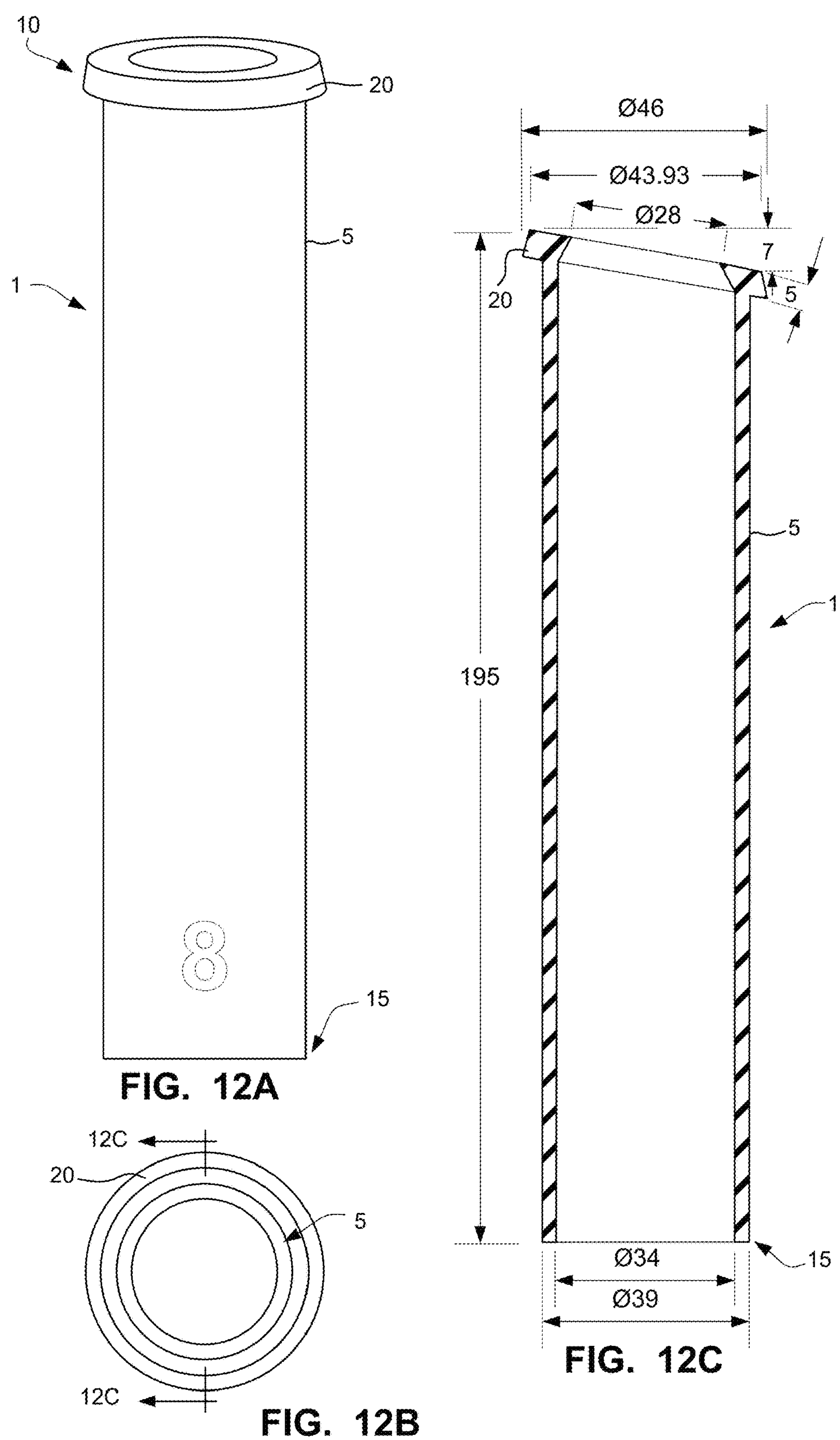
FIGS. 12A-12C illustrate views of an eighth size of a medical device according to an example of the present technology.
Figures 13A, 13B, 13C:
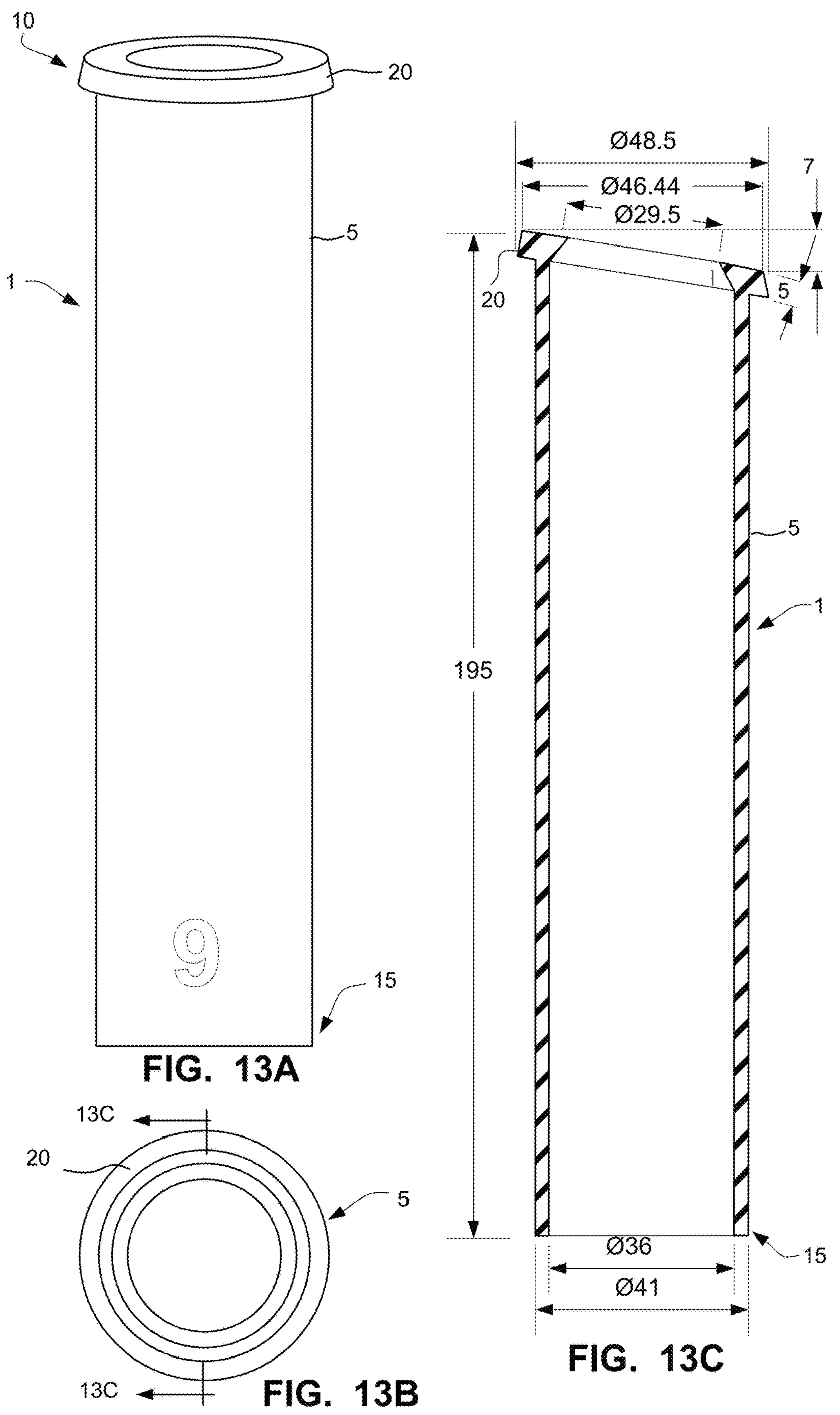
FIGS. 13A-13C illustrate views of a ninth size of a medical device according to an example of the present technology.
Figures 14A, 14B, 14C:
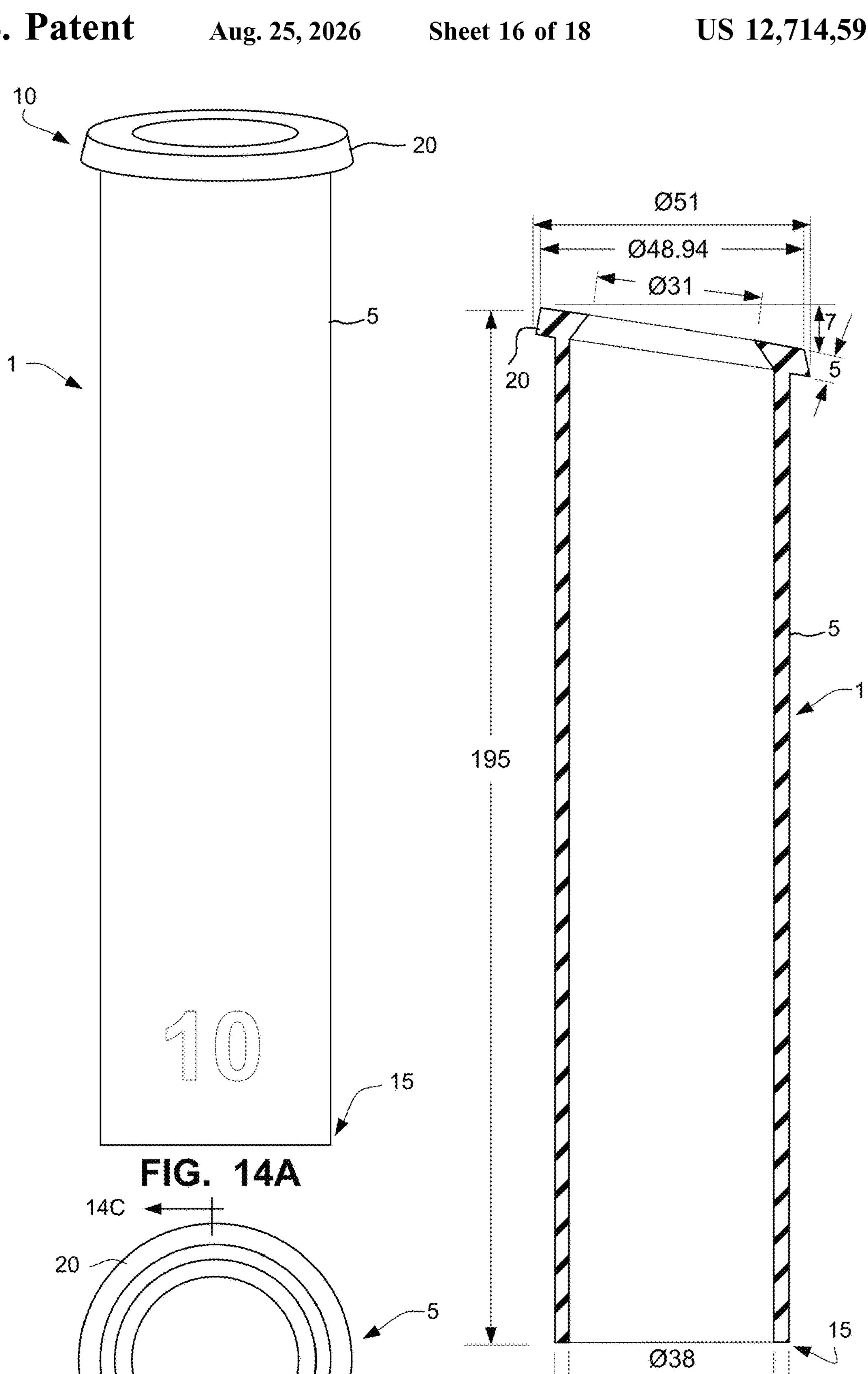
FIGS. 14A-14C illustrate views of a tenth size of a medical device according to an example of the present technology.

Due to variations in human anatomy, a physician may find it to be beneficial to have a plurality of different sizes of sleeves, in order to best fit the user or patient at hand. Thus, a kit for post procedural treatment for penile enhancement, including a plurality of flexible sleeves may be provided. The kit may include 2-15 different sized sleeves, e.g., 3 sizes or 10 sizes. As shown in FIGS. 5A-14C, showing 10 different sizes, each sleeve may be labeled with a size, e.g., "1", "2", "3", etc., to assist the physician in selecting the appropriately sized sleeve for a given patient or user. Each sleeve may a different inner diameter but substantially the same length and/or the same thickness. FIGS. 5A-14C show exemplary dimensions (in mm) which can vary up to 5-20 percent from what is shown. For convenience, FIGS. 5A to 14C have been labelled with reference numbers similar to those shown in FIGS. 1 to 3. FIGS. 5B, 8B, 9B, 10B, 11B, 12B, 13B and 14B show the bottom view of the sleeve, and FIGS. 6B and 7B show the top view of the sleeve.

Increased Penis Print in a Natural Looking Way

Figures 22, 23, 24:
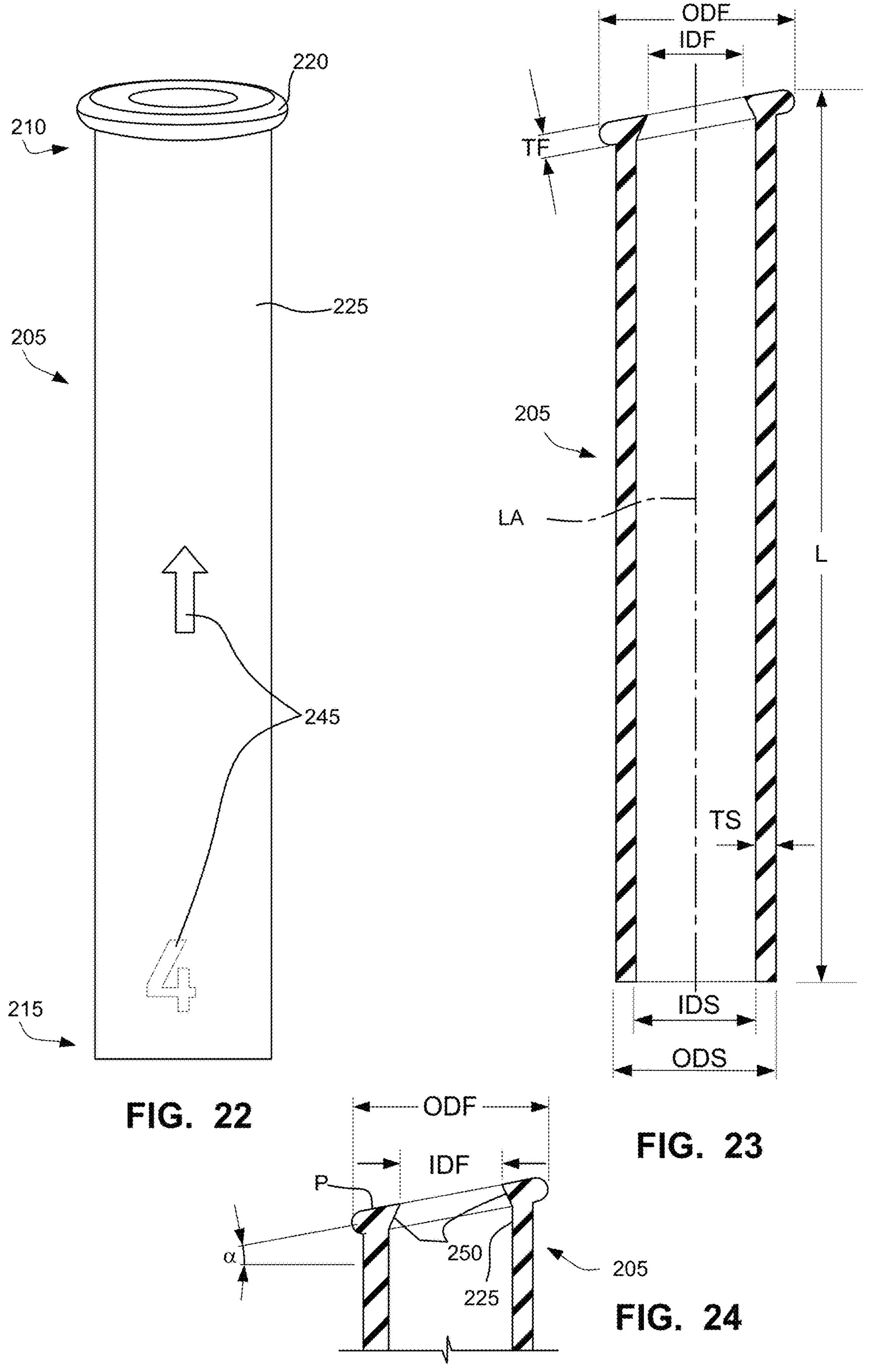
FIGS. 22-24 illustrate sleeve according to yet another example of the present technology.

FIGS. 22-24 illustrate a sleeve 205 in accordance with an alternative embodiment of the present technology. The sleeve may be used for non-medical use, such as by wearing the sleeve while wearing clothes. While the clothes will typically fully cover the penis while wearing the sleeve, an imprint of the sleeve will sometimes be able to show through the garment, such as a bathing suit, underwear, tights, shorts, pants, etc. When the imprint of the sleeve 205 shows through the garment, it is desirable to have the sleeve look as natural as possible and not artificial, thus giving the impression that the penis is larger than it actually is.

The sleeve 205 has a sleeve wall that may include a distal end 210 and a proximal end 215. The proximal end 215 is sized and configured to be positioned over the base of the penis. The sleeve 205 is configured and sized to extend from the base of the penis and along the body of the penis, leaving the head of the penis uncovered. The distal end 210 is sized and configured to terminate just below the corona of the glans of the penis, similar to what is shown, for example, in FIGS. 4E-4F. However, the sleeve 200 could be dimensioned to only extend from the distal end 210 towards but short of the base of the penis, e.g., over 50-75%.

The sleeve may have a closed loop shape in cross section, as seen in FIGS. 22-24. The sleeve 205 may have a solid wall portion from the distal end to the proximal end, e.g., with substantially no openings or interruptions. However, the sleeve may have other shapes, such as a C-shape cross section with a longitudinal opening or slot which would allow fitting of the penis into the slot in a lateral direction by resiliently stretching the C-shape and allowing it to return at least partially to the non-stretched shape to snugly fit around the penis.

The distal end may include a flange 220 that extends radially outwards from an outer surface 225 of the sleeve 205. As seen in FIGS. 22-24, the flange 220 has a rounded shape that simulates the shape of corona of the glans of the penis to provide a more natural look especially as seen through the wearer's clothing or garments. The flange extends radially outwards from an outer surface of the sleeve wall, the flange having an exterior side surface with a curved shape configured to match the shape of the corona of the glans of the penis. The flange thickness TF is about 4-7 mm, e.g., 5 mm, and may have a part circular or semi-circular shape, meaning the radius of curvature of the exterior part of the flange 220 is between 2-3 mm, e.g., 2.5 mm radius. As shown in FIGS. 22-24, the top of the sleeve 205 is relatively flat and smoothly transitions to a curved side wall of the flange. The top of the sleeve is configured to abut or lie adjacent or below the corona of the glans of the penis and the flange 220 radially extends outward of and as an extension of the corona, thus giving the impression of increased diameter in a natural way. Thus the imprint of the corona on the inside of the wearer's clothes shows on the outside of the wearer's clothes or garments.

The thickness TS of the sleeve 205 is about 0.5 mm to about 10 mm from the distal end to the proximal end, not including the flange 220. However, to further increase the appearance of the thickness of the penis, the side wall thickness could be from about 3 to about 15 mm or 8 to about 12 mm whilst still allowing the sleeve to stretch and/or roll over the penis when donned or removed. As would be apparent, this means that the effective diameter is increased to about 6-30 mm, e.g., 16-24 mm, the difference between the inner diameter IDS and the outer diameter ODS. In examples the thickness TS of each side wall is about 4 mm to about 5 mm or 4.5 mm as shown in FIG. 23. The ODS is in the range of 30-40 mm (e.g., 35 mm) and the IDS is in the range of 20-30 mm (e.g., 25-27 mm).

The thickness TS could vary based on the diameter of the sleeve 205, or the thickness can remain constant regardless of the diameter (e.g., inner diameter IDS) of the sleeve, as described in relation to the kit of sleeves below. This thickness (e.g., 3.5 mm to 5.5 mm) or range of thicknesses has been found to be beneficial, e.g., in terms of allowing the sleeve to be manipulated and/or providing medical benefits to the user, as described herein. For example, this thickness allows for the sleeve to be rolled and stretched during placement on the penis, and yet is still firm or rigid enough to hold the penis extended without having folds or "wrinkles" in the sleeve to provide a more natural look when imprinted from the interior of the wearer's clothes. The sleeve may be relatively more rigid in the axial direction, and relatively more flexible in the circumferential direction. In addition, the thickness TS of the sleeve 205 could vary along the longitudinal axis LA, e.g., the thickness at the proximal end could be more than the thickness at the distal end, and gently tapered therebetween.

The inner diameter IDS of the sleeve is about 15-50 mm, or it may be about 20-40 mm. The inner diameter IDS may be 20 mm, 22 mm, 24 mm, 26 mm 28 mm, 30 mm, 32 mm, 34 mm, 36 mm or 38 mm. Larger sizes are available as well, including 40 mm, 42 mm, 44 mm, 46 mm, etc.

A length L of the sleeve is about 180-220 mm, e.g., about 195 mm, when extending from the base to the penis to the glans. However, the length could be shortened to only extend from the distal end 210 towards but short of the base of the penis, especially if the wearer is not interested in penis lengthening but only interested in girth enhancement. For example, the length could be as little as 40-100 mm.

The flange 220 is contained in a plane P that is angled at a flange angle a relative to a longitudinal axis LA of the sleeve 205. The flange angle a is about 1-15 degrees, or about 3-6 degrees. The angle is selected to match the shape of the corona of the glans of the penis. If no flange is provided, the distal end of the sleeve is preferably angled to so match.

An outer diameter ODF of the flange 20 is about 2-15 mm, e.g., 6-10 mm (e.g., 8 mm) greater than the outer diameter ODS of the sleeve, spaced axially away from the flange 220. In an example, an inner diameter IDF of the flange 220 is less than an inner diameter IDS of the distal end 10 of the sleeve 20. Making the inner diameter less than the sleeve diameter should help to prevent the head of the penis from retracting into the sleeve.

In an example, a thickness TF of the flange 220 is about 2-8 mm, e.g., about 5 mm.

A superior portion of the sleeve may be marked with an indicator or indicia 245, e.g., a logo and/or an arrow, to help the user or physician mount the sleeve 205 in the correct position on the user's penis. For example, the indicia 245 is positioned about a superior (top) surface of the penis that faces upwards when the user is in a standing position. The indicia 245 helps to align the flange 220 in the correct position relative to the corona of the glans of the penis. In another example, the indicia may be a line on the inner surface of the sleeve that is revealed when the sleeve is rolled. In another example, the top surface of the flange may include an alignment mark or arrow, as the flange is always visible even if the sleeve is rolled.

The inner diameter IDF of the flange 220 includes an inwardly angled portion 250 that forms an angle relative to an inner surface 255 of the sleeve adjacent the flange. In an example, the angled portion 250 forms a part of a cone, e.g., a truncated cone having a base diameter that is greater than the top diameter. In an example, the cone is asymmetric. The cone shape helps to prevent the penis from retracting into the sleeve. The IDF may range from 20-25 mm (e.g., 21.5 mm), and the ODF may rent for 35-28 mm, e.g., 42 mm.

The sleeve 205 can be mounted on the penis as described above, e.g., rolled on. Alternatively, the sleeve 205 can include a longitudinal slot allowing lateral insertion of the penis.

The materials and properties of the sleeve 205 may be in the ranges described above in relation to Table 1.

WRAP—Variable Circumference

In addition, a sleeve 100 can be mounted on the penis in a way that is different than that shown in FIGS. 4A-4F and by extension FIGS. 22-24. For example, the sleeve 100 can be separated along its longitudinal axis such that the sleeve has first 102 and second longitudinal edges 104. The sleeve may be wrapped around the penis, and secured. The sleeve may be formed of a textile material, as described above.

Figures 15, 16, 17, 18, 19, 20, 21:
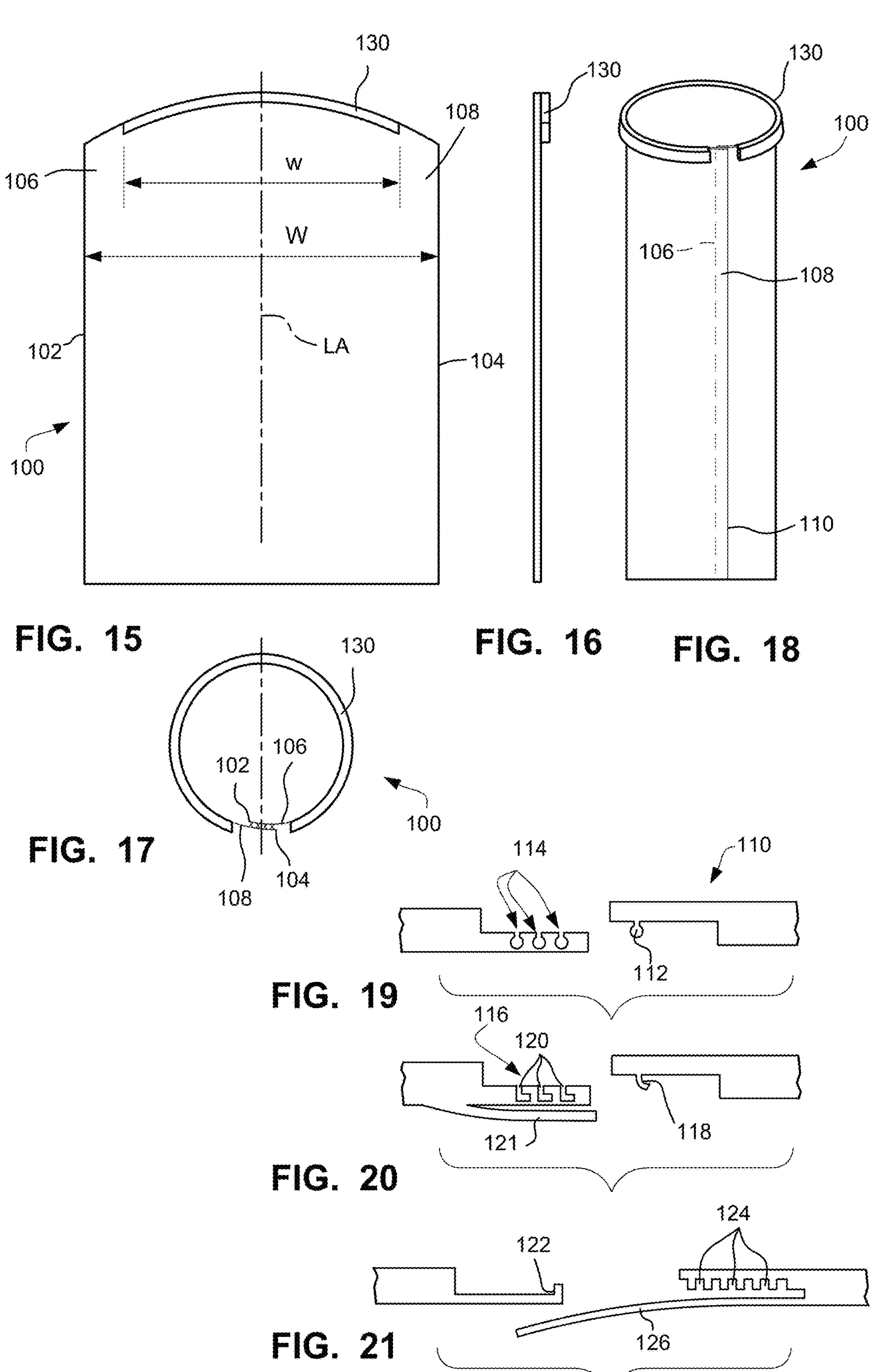
FIGS. 15-18 show a variation of a medical device or sleeve according to the present technology.
FIGS. 19-21 illustrate examples of how marginal edges (or flanges) of the sleeve shown in FIGS. 15-18 can be releasably connected.

As shown in FIG. 15, the sleeve may start as a substantially flat sheet. However, the top of the sheet may have a curved shape, such that when wrapped about the penis, the top part is at an angle that is configured to match the shape of the corona of the glans, as described above. The sheet may have the thickness as described above in relation to the wall thickness TS of the sleeve. The sleeve may also have a length that is similar to the length L described in FIGS. 1-3. The sleeve may be cut to appropriate length before wrapping around the penis.

When wrapped, margins 106, 108 of the longitudinal edges 102, 104 at least partially overlap as shown in FIGS. 17-18. The overlapping margins 106, 108 can be releasably attached and connected in a number of different manners, e.g., zipper, hook and loop fastener (e.g., VELCRO®), adhesive (e.g., biocompatible adhesive), one or more snaps, etc. Moreover, the material of the sleeve may have an adhesive property. The edges may also be permanently attached or affixed. FIG. 18 shows that one margin, e.g. 108, covers the other margin 106 (shown in hidden lines). The margin 108 forms a seam 110 that is located on the outer surface of the sleeve.

FIG. 17 schematically shows that the margins 106, 108 include a hook and loop fastener (hooks and loops) or adhesive, indicated as xxx. FIG. 19 shows that the margins may include a snap arrangement 110 including at least one protruding snap 112 and one or more snap recesses 114. FIG. 20 shows a hook and eye arrangement 116 (such as the type used for a women's brassiere), including at least one hook 118 and at least one hook recess 120 or loop. As shown in FIG. 20, the margin with the recess 120 or loop may also include a flap 121 that helps protect the user's skin from the hook 118. The flap 121 may be integrally formed in one piece with the margin, or it may be that the flap is made of a different material (e.g., textile), while the margin with the recesses can be made of another material, e.g., silicone. FIG. 21 shows an arrangement where one of the margins 106, 108 includes a protrusion 122 and the other margin includes a plurality of recesses 124. FIG. 21 also shows that one of the edges includes a flap 126 that surrounds an outer surface of the marginal edge, creating a sandwich type structure. The flap may be affixed to the edge via adhesive and/or hook and loop. In some forms, a plurality of such fasteners (e.g., 2, 3, 4, 5, 6 or more) could be provided along the seam or longitudinal axis to attach the edges or margins to one another.

As is apparent from the above description, the circumference or diameter of the sleeve can be adjusted to a size that is appropriate for the wearer's penis, e.g., by stretching in the circumferential direction and connecting the margins once the sleeve reaches the appropriate circumference. The circumference of the sleeve will preferably be slightly less than the circumference of the penis, to allow for appropriate compression. This might be helpful so that it is not necessary to provide as many different sizes, compared to FIGS. 5A-14C. However, different sizes of the sleeve shown in FIG. 15 can also be provided, similar to FIGS. 5A-14C. FIG. 15 shows the exterior surface of the sleeve.

The sleeve may include a flange 130 as described above, but it need not have a flange. The flange is shown in FIGS. 15-18. The flange may be dimensioned such that it has a width w that is less than the width W of the sleeve, as shown in FIGS. 15, 17 and 18. This is helpful as it allows some variation in the distance the margins overlap, and the circumferential ends of the flange will not interfere with one another. However, the ends of the flange could also be connected as shown in FIGS. 19-21. In an example, the flange can be made of medical grade silicone and molded (e.g., insert molded) onto the sleeve, which can be made of a textile. Alternatively, the flange could be in the form of a silicone bead that is applied to the top edge of the textile material.

Different features, variations and multiple different examples have been shown and described with various details. What has been described in this application at times in terms of specific examples is done for illustrative purposes only and without the intent to limit or suggest that what has been conceived is only one particular example or specific examples. It is to be understood that this disclosure is not limited to any single specific example or enumerated variations. Many modifications, variations and other examples will come to mind of those skilled in the art, and which are intended to be and are in fact covered by both this disclosure.

While the present technology has been described in connection with what is presently considered to be some practical and preferred examples, it is to be understood that the present technology is not to be limited to the disclosed examples, but on the contrary, is intended to cover various modifications and equivalent arrangements included within the spirit and scope of the disclosure.

The invention claimed is:

1. A sleeve for placing on a human penis, the sleeve consisting of:

a flexible sleeve consisting of a single layer of silicone, the sleeve having a sleeve wall having a proximal end and a distal end, the sleeve wall being configured and sized to extend from just below the corona of the glans of the penis and along the body of the penis towards the base of the penis, wherein the distal end includes a flange that extends radially outwards from an outer surface of the sleeve wall, the flange having an exterior side surface with a curved shape configured to match the shape of the corona of the glans of the penis, wherein the sleeve wall has a thickness spaced away from the flange along a longitudinal axis of the sleeve of about 0.5 mm to about 10 mm from the distal end to the proximal end, not including the flange, wherein the flange is contained in a plane and the plane is angled about 1-15 degrees relative to the longitudinal axis of the sleeve.

2. The sleeve of claim 1, wherein the flange is about 5 mm in thickness, and wherein the thickness of the sleeve wall spaced away from the flange along a longitudinal axis of the sleeve is about 3 mm to about 10 mm.

3. The sleeve of claim 1, wherein an inner diameter of the sleeve wall is about 15-50 mm.

4. The sleeve of claim 3, wherein the inner diameter is about 20-40 mm.

5. The sleeve of claim 1, wherein a length of the sleeve wall is about 180-220 mm.

6. The sleeve of claim 1, wherein the sleeve wall is configured to be moved from an unrolled positioned to a rolled position by rolling the proximal end radially outwards and axially towards the distal end.

7. The sleeve of claim 6, wherein, in the rolled position, the sleeve wall is stretchable from a first diameter to a second diameter.

8. The sleeve of claim 1, wherein the exterior side surface is substantially in the shape of a semi-circle having a radius in a range of about 2-3 mm.

9. The sleeve of claim 1, wherein an inner diameter of the flange is less than an inner diameter of the distal end of the sleeve wall.

10. The sleeve of claim 1, wherein a diameter of the flange is about 2-10 mm greater than an outer diameter of the sleeve wall spaced axially away from the flange.

11. The sleeve of claim 1, wherein a thickness of the flange is about 2-8 mm.

12. The sleeve of claim 11, wherein the thickness of the flange is about 5 mm.

13. The sleeve of claim 1, wherein an inner diameter of the flange includes an inwardly angled portion in the form of a cone that forms an angle relative to an inner surface of the sleeve adjacent the flange.

14. The sleeve of claim 1, wherein the sleeve wall has a closed loop shape in cross section, and the sleeve wall has a solid wall portion from the distal end to the proximal end with substantially no openings or interruptions.

15. The sleeve of claim 1, wherein the sleeve is configured to compress and/or elongate the penis.

16. A device for placing on a human penis, the device consisting of:

a flexible sleeve consisting of a single layer of homogeneous material, the sleeve having a proximal end and a distal end, the sleeve not covering the head of the penis and being configured and sized to extend from the corona of the glans of the penis and along the body of the penis towards the base of the penis, wherein the distal end includes a flange that extends radially outwards from an outer surface of the sleeve, and wherein a sleeve wall thickness of the sleeve spaced away from the flange along a longitudinal axis of the sleeve is about 0.5 mm to about 10 mm from the distal end to the proximal end, not including the flange, wherein the flange is contained in a plane and the plane is angled about 1-15 degrees relative to the longitudinal axis of the sleeve, and wherein the flexible sleeve is made of silicone.

17. The device of claim 16, wherein the wall thickness is about 1 mm to about 4 mm.

18. The device of claim 16, wherein the wall thickness is about 4 mm.

19. The device of claim 16, wherein an exterior surface of the flange has a curved shape.

20. A device for placing on a human penis, the device consisting of:

a flexible sleeve consisting of a single layer of silicone, the sleeve having a proximal end and a distal end, the distal end being sized and dimensioned to extend just below the corona of the glans of the penis towards the base of the penis, wherein the sleeve from the distal end to the proximal end has a closed loop shape in cross section, and has a solid wall portion with substantially no openings or interruptions, wherein the sleeve has a longitudinal axis and is rollable along the longitudinal axis, wherein the distal end includes a flange that extends radially outwards from an outer surface of the sleeve, wherein the flange is about 2-8 mm in thickness, and wherein a thickness of the sleeve spaced away from the flange along a longitudinal axis of the sleeve is about 0.5 mm to about 10 mm, and wherein an outer diameter of the flange is about 2-10 mm greater than an outer diameter of the sleeve wall spaced axially away from the flange.

21. The device of claim 20, wherein an exterior surface of the flange has a curved shape.

* * * * *